United States Patent [19]

Seppi et al.

[11] 4,182,311
[45] Jan. 8, 1980

[54] METHOD AND SYSTEM FOR CARDIAC COMPUTED TOMOGRAPHY

[75] Inventors: Edward J. Seppi, Menlo Park; George S. Harell, Portola Valley; Charles C. Morehouse, Cupertino, all of Calif.

[73] Assignee: Varian Associates, Inc., Palo Alto, Calif.

[21] Appl. No.: 789,910

[22] Filed: Apr. 22, 1977

[51] Int. Cl.$^2$ .............................................. A61B 6/02
[52] U.S. Cl. .............................. 128/653; 250/363 S; 250/445 T
[58] Field of Search .......................... 128/2 A, 2.05 Z; 250/401–403, 445 T, 320, 323, 363 R, 363 S

[56] References Cited

U.S. PATENT DOCUMENTS

| | | | |
|---|---|---|---|
| 3,778,614 | 12/1973 | Hounsfield | 250/362 |
| 3,871,360 | 3/1975 | Van Horn et al. | 128/2.08 |
| 3,952,201 | 4/1976 | Hounsfield | 250/403 |
| 3,954,098 | 5/1976 | Dick et al. | 128/2 V |
| 4,032,789 | 6/1977 | Workman | 250/402 |
| 4,033,335 | 7/1977 | Nickles | 128/2 A |
| 4,037,585 | 7/1977 | Gildenberg | 128/2 A |
| 4,042,811 | 8/1977 | Brunnett et al. | 250/445 T |
| 4,045,815 | 8/1977 | Griffith et al. | 128/2.06 G |

OTHER PUBLICATIONS

O'Reilly, R. J. et al., "Automatic Computer Analysis of Digital Dynamic Radionuclide Studies of the Cerebral Circulation," Jrnl. Nuclear Medicine, V. 13, Sep. 1972 #9, pp. 658–666.

Primary Examiner—Robert W. Michell
Assistant Examiner—Francis J. Jaworski
Attorney, Agent, or Firm—Stanley Z. Cole; Leon F. Herbert

[57] ABSTRACT

System and method are set forth enabling reconstruction of images of desired "frozen action" cross-sections of the heart or of other bodily organs or similar objects undergoing cyclic displacements. Utilizing a computed tomography scanning apparatus data is acquired during one or more full rotational cycles and suitably stored. The said data corresponding to various angular projections can then be correlated with the desired portion of the object's cyclical motion by means of a reference signal associated with the motion, such as that derived through an electrocardiogram—where a heart is the object of interest. Data taking can also be limited to only the times when the desired portion of the cyclical motion is occurring. A sequential presentation of a plurality of said frozen action cross-sections provides a motion picture of the moving object.

8 Claims, 4 Drawing Figures

TO CONTROL
AND IMAGE
RECONSTRUCTION
STATION 20

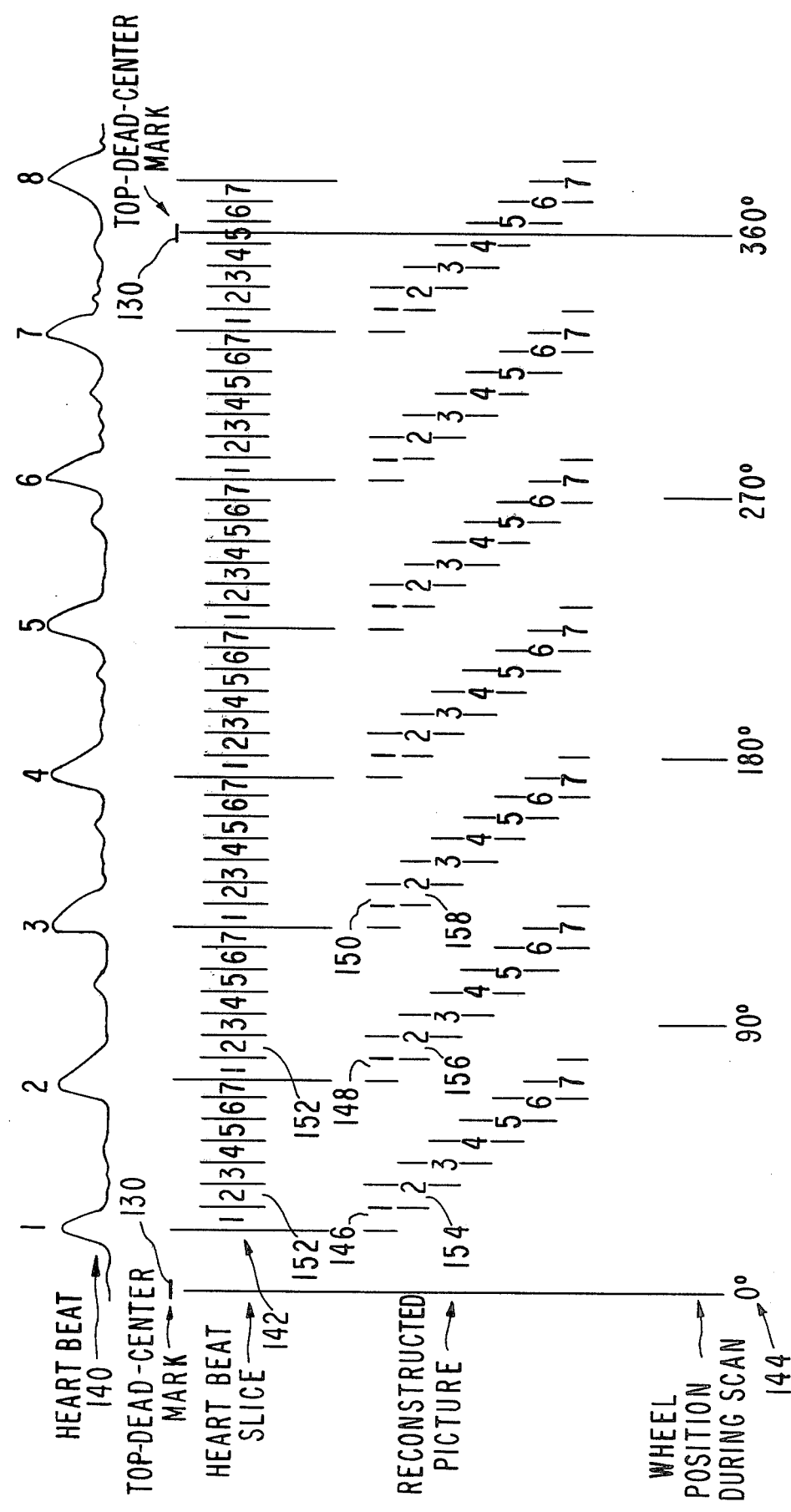

METHOD AND SYSTEM FOR CARDIAC COMPUTED TOMOGRAPHY

BACKGROUND OF INVENTION

This invention relates generally to medical diagnostic apparatus and methodology and more specifically relates to X-ray scanning apparatus and methodology of the type associated with computed tomography.

Within recent years, much interest has been evidenced on the part of medical diagnosticians in the field now widely known as "computed tomography." In a typical procedure, an X-ray source and detector apparatus are positioned on opposite sides of the portion of the patient which is intended for examination. In early prior art these paired elements are made to transit across the body portion to be examined while the detectors measure the X-ray absorption at the plurality of transmission paths defined during the transit process. Periodically as well, the paired source and detector means are rotated to a different angular orientation about the body and the transit process repeated. A very high number of absorption values may be yielded by procedures of this type and the relatively massive amounts of data thus accumulated are processed by a digital computer which cross-correlates the absorption values to thereby derive absorption values for a very high number of points (typically in the thousands) within the section of the body being scanned. This point by point data can then be combined to enable reconstruction of a matrix (visual or otherwise) which constitutes an accurate depiction of the density function of the bodily section examined. The skilled diagnostician, by considering one or more of such sections, can often diagnose various bodily ailments such as tumors, blood clots, etc.

Later developments in the computed tomography field are demonstrated in the copending application of John M. Pavkovich and Craig S. Nunan, Ser. No. 643,894, filed Dec. 23, 1975 and entitled "Tomographic Apparatus and Method for Reconstructing Planar Slices From Non-Absorbed Radiation," and in the copending application of John M. Pavkovich entitled "Apparatus and Method for Reconstructing Data" filed Dec. 23, 1975 under Ser. No. 643,896. Both of these applications are assigned to the same assignee as is the present application.

The apparatus disclosed in the last cited applications utilizes a fan beam source of radiation coupled with application of a convolution method of data reduction with no intervening reordering of fan rays, to thereby eliminate the errors and delay in computation time which would otherwise be involved in such reordering. The radiation source and detector means are positioned on opposed sides of the portion of the patient being examined and these elements are made to rotate through a revolution or portion thereof while the detectors measure the radiation absorption at the plurality of transmission paths defined during the rotational process.

In a typical apparatus embodiment of the Pavkovich et al type of apparatus, an assembly is provided which is rotatable about an axis extending along a central opening defined therein, together with means for positioning the bodily portion to be examined within a central opening so that the axis of assembly rotation is perpendicular to a thin, generally planar section of the body portion being scanned. A source of penetrating radiation, i.e., of X-rays or gamma rays is mounted on the assembly toward one side thereof a provides radiation in the form of a fan beam. Means are provided for rotating the assembly so that the fan beam impinges upon the bodily portion at a plurality of incident directions. Detection is enabled by means positioned on the assembly opposite the source, which thus detects non-absorbed radiation proceeding laterally along the section.

In general, computed tomography apparatus of the foregoing type has found its principal application to examination of bodily structures or the like which are in a relatively stationary condition. For example, currently available computed tomographic apparatus yields tomographic images of the beating human heart which suffer from degradation because of cardiac motion.

SUMMARY OF INVENTION

Now in accordance with the principles of the present invention, a system and method is provided which enables highly effective "stop action" or "frozen" images to be generated of cross-sections through organs of the body or the like undergoing cyclic displacements as, for example, images of the human heart during selected phases of the cardiac cycle.

Pursuant to the present invention, and utilizing computed tomography apparatus of the aforementioned type, raw projection data is collected in consequence of one or more continuous cycles of rotation of the scanner portion of the said apparatus, the said data being stored for use in the reconstruction process. By suitable correlation of the stored data with that portion or phase of the cyclic movement for the body organ which is to be examined, the desired cross-sectional image may be reconstructed. In addition, animated presentation is obtained by rapidly projecting cross-sections of sequential positions of the object throughout its cycle of movement.

In order to enable this correlation, means are provided for positively identifying the gathered data with portions of the organ cycle. In the case of the heart, for example, the ECG signal may be appropriately identified with the scanner projection angle, as for example, by means directly marking the ECG record with indicia representing the associated projection angle; or the ECG reference points may be included with the stored data or separately stored so that same may be thereafter identified with the projection angles corresponding to the portion of the cycle sought to be investigated.

In application of the invention to analysis of a cardiac cycle, the R—R interval for each cardiac cycle is typically subdivided into seven equal segments. Within any cycle the segments are all of equal length. The CT angle for projections corresponding to the same segment from each of the cardiac cycles are then identified, i.e., by the techniques aforementioned. In reconstructing the final seven images, however, the angular projections from two successive segments in each of the recorded beats are preferably utilized, as such procedure yields a considerable increase in number of available projections, thereby substantially improving generation of image density data—with resultant improvement in image "quality" without any severe degradation resulting from blurring. The number of angular projections available pursuant to the invention, may similarly be increased by increasing the total number of scan rotations utilized, e.g., to 3 or 4 or more.

In another aspect the data, instead of being taken throughout the rotational scanning, can be taken only at the times when the desired portion or portions of the cylical motion is occurring. This is particularly useful when only a single or relatively few cylical positions are known in advance to be the only positions of interest. Exposure to X-rays is minimized by this approach.

BRIEF DESCRIPTION OF DRAWINGS

The invention is diagrammatically illustrated, by way of example, in the drawings appended hereto, in which:

FIG. 4 is a graphic representation of a reconstruction technique utilizable in accordance with the present invention.

DESCRIPTION OF PREFERRED EMBODIMENT

Figure 1:
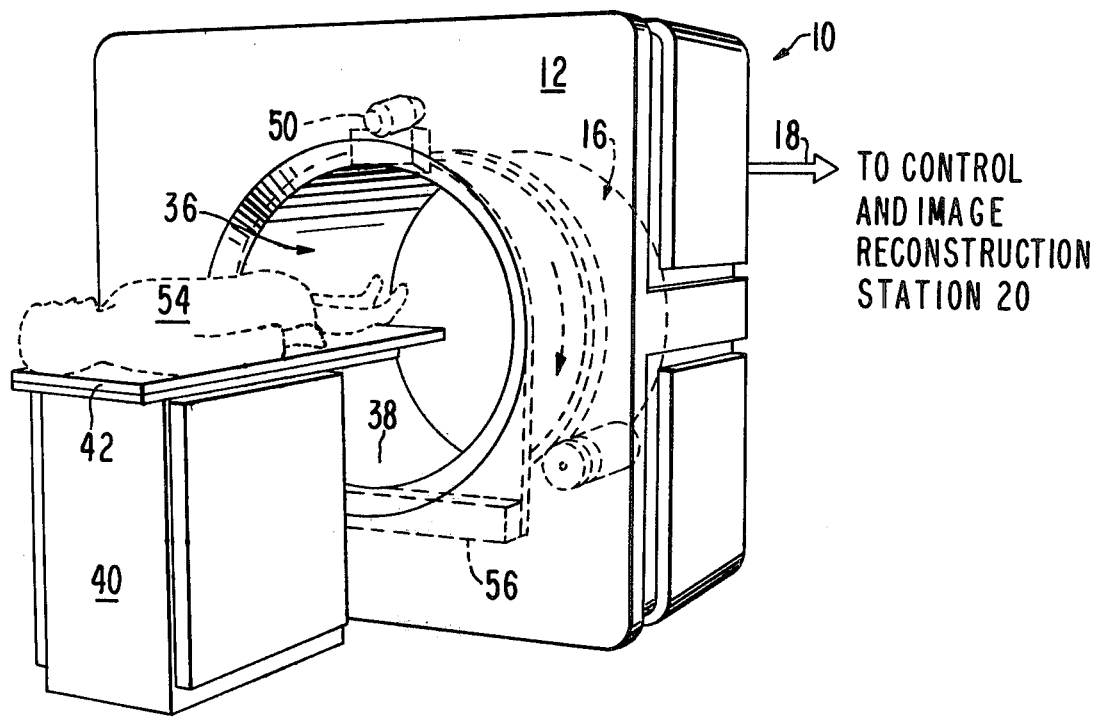
FIG. 1 is an external perspective view, schematic in nature, of typical scanning apparatus with which the present invention may be utilized.

In FIG. 1 herein an external perspective view appears, the view being somewhat simplified in nature, and setting forth scanning apparatus 10 of a type suitable for use with the invention. This view may be considered simultaneously with FIG. 2. In general, these Figures disclose only prior art details of the devices illustrated therein, and will serve primarily to establish an environment for illustrating the present invention.

Figure 2:
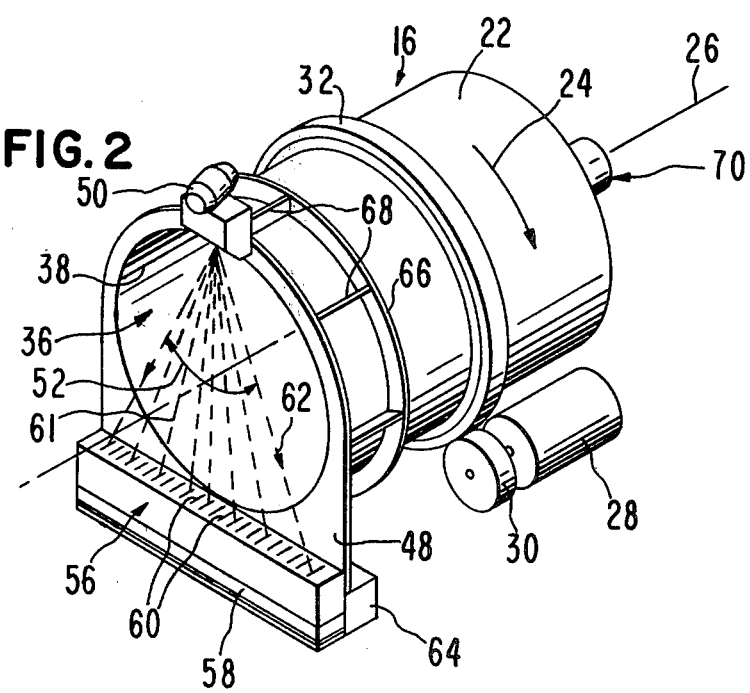
FIG. 2 is a perspective view, again somewhat schematic in nature, depicting the rotatable assembly portion of the FIG. 1 apparatus.

Apparatus 10 comprises generally an external casing 12, within which a frame (not seen) supports a rotatable assembly 16, better seen in FIG. 2. Scanning apparatus 10 forms part of a computed tomography system, the remaining elements of which principally include control, image reconstruction elements, and image display elements, most of which are contained at a control and image reconstruction station. Apparatus 10 is in communication with the said station by various control lines, as schematically indicated at link 18 in FIG. 1, which is to say that digital information developed in consequence of the scanning operations effected by apparatus 10 are furnished to such station; and the latter in turn provides both control information for actuating apparatus 10, as well as the various power and excitation potentials, e.g., for the radiation source, the motor, and for other elements which are present in said apparatus.

Rotatable assembly 16 includes an outer cylinder 22 of stainless steel or other metal, and is adapted to be rotated in direction 24 about its central axis 26 by means of a motor 28, the drive wheel of which bears against a drive collar 32 secured about cylinder 22. Wheel 30 may thus include a rubber surface 34 or the like which by virtue of its high coefficient of friction is effective in causing non-slip rotation of cylinder 22. Other drive mechanisms may be similarly utilized. For example, a timing belt driven by motor 28 may engage with a suitable track about cylinder 22 to effect the desired rotation.

The central opening 36 of assembly 16 serves to receive a patient 54 who is to be examined within apparatus 10. A sleeve 38 of plastic or the like, is secured to casing 12 and provides a stationary reference frame— which has certain advantages, especially psychologically, for the patient who is positioned within opening 36.

The patient 54 during use of apparatus 10 is positioned upon the top surface 42 of a positioning bench 40, the surface 42 being movable along axis 26 so as to enable movement of the patient into such apparatus. Bench 40 may include actuating means which enable incremental advance of same so as to facilitate successive transverse scan sections through the body of patient 54. The advance of the patient can in some instances also be continuous. Such means can also enable movement of the bench in other directions to facilitate the patient positioning.

The forward end of assembly 16 carries a plate 48 at the periphery of which is mounted a radiation source 50, preferably comprising an X-ray source capable of projecting an X-ray pattern in the form of fan beam 52. Fan beam 52 may be yielded by collimator 51 which is positioned in front of the X-ray emission source, as is known in the art. Fan beam 52 is preferably (though not necessarily) at least as wide as the object to be examined which in the present instance constitutes patient 54.

A collimator/detector assembly generally indicated at 56 and consisting of a detector means 58 and a collimator means 60, is mounted directly opposite source 50, i.e., toward the opposite edge of plate 48. Although other types of detectors suitable for use with X-rays and similar electromagnetic radiation may be utilized such as crystal scintillators coupled with photomultipliers or photodiodes and so forth, detector means 58 preferably comprises an array of ionization chambers, effectively located in side-by-side relationship and aligned with respective passageways formed by the collimator means 60, which chambers may be of the xenon or the xenon-krypton type. Detector means 58 is in very close physical proximity to a signal processing and conditioning means 64. This close proximity has important advantages in minimizing the possibility of introducing spurious signals into the various detector channels which can arise from the high potentials associated with the X-ray source or the like.

In the case of X-ray diagnosis, the thickness of fan beam 52 as defined by the collimators is typically between about 1 mm and 15 mm at the middle of the object. It will be understood that as the source-detector array undergoes relative rotation with respect to the patient, (continuously where exact reconstruction is desired) over a time of approximately 1 to 15 seconds, readings of absorbed radiation are measured by detector means 58. Typically, for example, on the order of 301 individual detector cells may constitute the detector array 58, which cells are effectively in side-by-side relationship. Typically, therefore, a set of measurements may be taken at each successive one degree increment of rotation (preferably by pulsing the source on at each said one degree position), so that 360×301 values of measured (transmitted) radiation are obtained during each 360 degree cycle or rotation. Pursuant to the present invention, the data acquisition may be completed during one relative rotation, i.e., 360 degrees (of the system); however, more commonly pursuant to the invention, several successive and continuous rotations (i.e. each rotation is continuous and there is not stoppage between successive rotations) will be involved in the data acquisition process.

In the normal course of operating systems of the type thus far discussed, data from the collimator/detector assembly 56, after suitable processing and conditioning, is provided to the control and image reconstruction station, and if a cross-sectional image is to be directly obtained the said data is convolved and appropriately stored and later back projected with other data to provide an output picture which is a replica of the thin cross-section of patient 54 which has been examined. It will, of course, be understood that the data need not necessarily be converted into a visually discernable picture, but can be expressed in other analytical forms, i.e., numerically or so forth.

Figure 3:
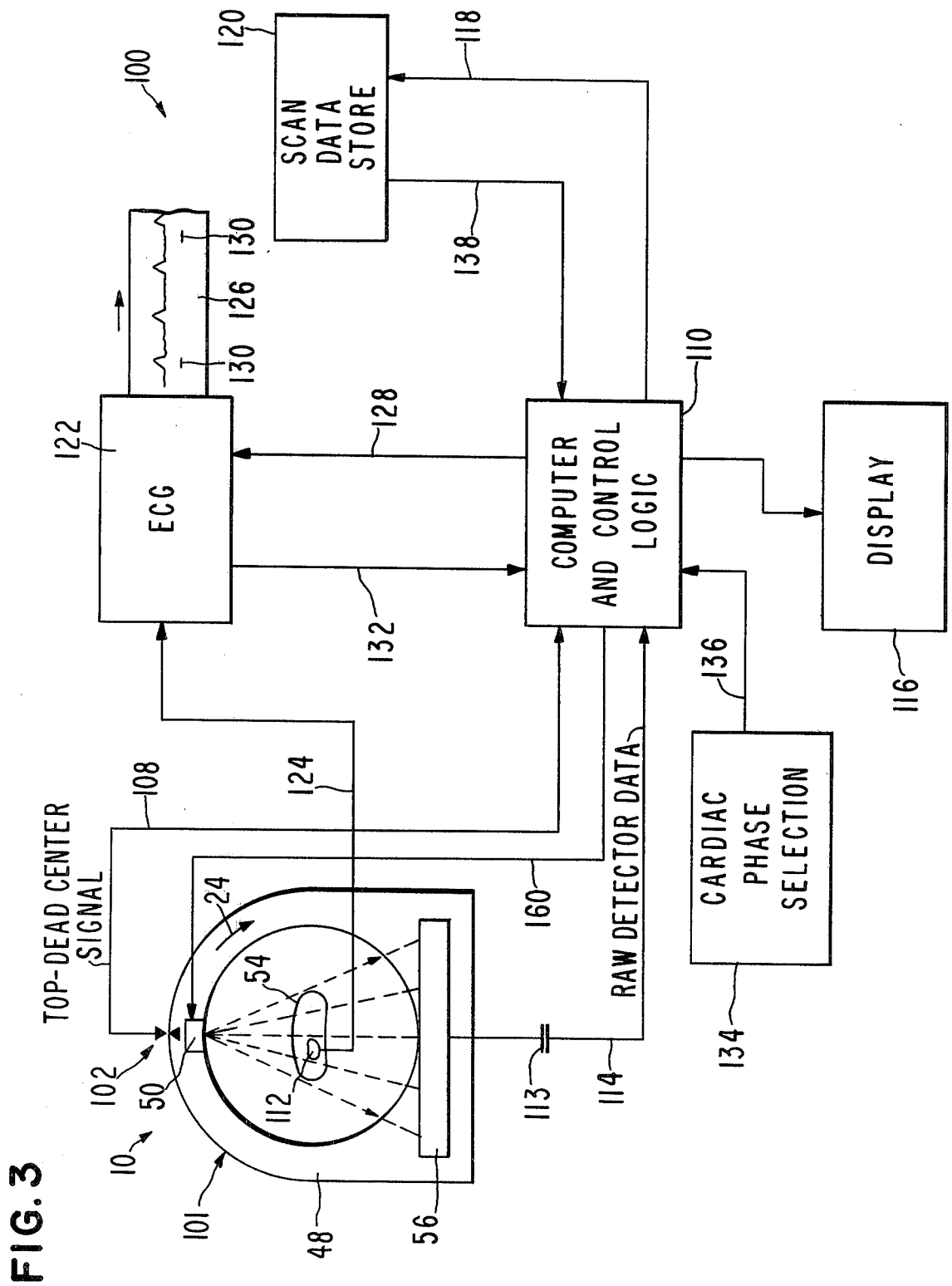
FIG. 3 is a schematic block diagram, illustrating operation of a representative system operating pursuant to the principles of the present invention.

In FIG. 3 herein a schematic block diagram is set forth illustrating a system 100 suitable for cardiac computed tomography pursuant to the principles of the present invention. System 100 is shown associated with a CT scanning apparatus 10 of the type heretofore discussed. In order to simplify and better illustrate operation of the invention, only the rotating plate 48 carrying the essential scanner elements appears in schematic fashion in the present Figure. These rotating elements, i.e., plate 48 and the components carried thereon (e.g., source 50 and the detector/scanner assembly 56) will for convenience be henceforth collectively identified as scanner 101.

Pursuant to one aspect of the present invention, center signal generating means are associated with scanner 101, as indicated schematically at 102. Such means may typically comprise a commercially available optical coupling. For example, a light source and detector may be positioned such that an optical barrier fastened in the rotating scanner 101 will periodically interrupt the light path between source and detector providing an electrical pulse in line 108 indicating "TOP DEAD CENTER" positioning of the scanner 101. As the scanner rotates in the direction 24, the TOP DEAD CENTER signal is thus enabled in line 108 each time the scanner reaches its vertical position. The signal, in turn, proceeds via line 108 and is provided to the computer and control logic means 110, which may form part of the control and image reconstruction station previously referred to.

In order to concretely illustrate operation of the present invention, it may be assumed that the object sought to be examined is the beating heart 112 of the patient 54 positioned within apparatus 10. Both patient and heart are, of course, shown in highly schematic fashion, the heart being very much enlarged in order to render the object clear. It may be noted here that in the "normal" operation of CT devices as previously discussed herein, cross-sectional views are taken by rotating scanner 101 through one or more 360 degree rotation and collecting data from detector array 58 for each of a plurality of angles about such cycle of rotation. For example, in a typical procedure as above discussed, such projections may be gathered at each successive one degree rotation, to thereby provide 360 sets of projection data for each full rotation. Since in a typical embodiment of apparatus of the type considered herein the detector array may include 301 detector cells, it will be evident that throughout the course of one rotation a total of 301×360 data values are gathered—and these in turn are provided via the line 114 to the computer and control logic 110 which effects the convolution and back projection processing of such data, and eventually provides a visual or other representation, for example at a display means 116. The data interfeed from the rotating scanner is enabled through a slip ring connection 113 in line 114.

If the conventional techniques above set forth are utilized, it is found in practice that the heart or other pulsating or cyclically moving organs or the like appear as an essentially blurred object, and in a form in which a diagnostician cannot recognize structural features or matters of interest. Ideally, the diagnostician, to the contrary, would desire to obtain "stop action" or static views of the heart in a cross-sectional mode of presentation—and especially would the diagnostician desire such stop action views to correspond to recognized phases of the cardiac cycle. Pursuant to the approach of the present invention, such result is completely enabled.

In accordance with one technique of the present invention, a "normal" scan is effected at apparatus 10, but the data proceeding via line 114 to computer and control logic 110 is not immediately processed to yield the desired images or sections through the heart. Rather such data is furnished via the line 118 to a scan data storage means 120, e.g., a magnetic disc or other known memory device. Specifically, such data may be stored for one or a plurality of 360 degree cyclic rotations of scanner 101. It is important in this connection to note that the pertinent data is thus acquired all at one time with the patient in place, after which the patient may be removed from the apparatus and discharged from the laboratory or so forth, with the knowledge that all data required for full analysis of any particular portion or phase of the cardiac cycle has been acquired. In other words, there is no requirement for maintaining the patient in place at the apparatus for further examination and analysis. The analysis, rather, can be made from the stored data, which pursuant to the invention is reconstructed in leisurely fashion to produce the desired views. It may also be noted in this connection that the present apparatus 10 is especially well adapted to this mode of operation, in that the said data can be acquired during successive continuing rotations, i.e., the apparatus 10 as is disclosed, e.g., in the patent application of Kendall Dinwiddie et al. Ser. No. 677,958, filed 4/19/76 and entitled "Tomographic Scanning Apparatus," renders clear that such a device can undergo continuous successive rotations while continuing to acquire data, this being a particular convenience insofar as the present type of operation is concerned.

The basic problem involved in reconstructing slices through the heart corresponding to various selected phases of the cardiac cycle, now involves a requirement for correlating the slice of interest, i.e., the slice associated with a particular point in time in the cardiac cycle, with the projections pertinent thereto.

In order to enable the said correlation, an ECG means 122 is coupled to the patient, as schematically indicated at 124, to provide a record of cardiac cycle against a time base. At the same time, the correlation with projection is enabled by means of the centering signal previously referred to as provided in line 108. In the simplest mode of operation of system 100, an ECG record is schematically shown at 126 advancing from the ECG means 122. The centering signal provided in the first instance from line 108 may be in turn provided from computer and control logic 110 via line 128 to the ECG means 122, so that a mark 130 is placed on the ECG record in correspondence to the scanner achieving its top dead center position. It will be understood that since the top dead center position of source 50 is known and the speed of rotation of the scanner 101 is known, the angular location of the source is known at any time.

Thus it will be clear that by this sort of procedure the ECG record 126, itself carries a direct indication or correlation between the phases of the cardiac cycle and the angular position of the scanner plate 48 which thus enables one to ascertain directly from the ECG record 126 those projection angles at which data was acquired bearing upon the cardiac cycle of interest. It may incidentally be noted in connection with the foregoing discussion, that conventional ECG apparatus may carry means for manually marking the record 126 (in the manner of the indicia provided at 130) which conventional means are commonly used by the physician for manually marking the points on the ECG record which he later wishes to investigate. In practice, therefore, the commercially available ECG devices may be readily modified to accommodate the mode of operation just discussed, in that the signal in line 128 (or in line 108) may simply be utilized to enable the same marking means as is already present in the commercially available ECG unit.

In addition to the technique just described, more sophisticated data identification methods may be utilized. Thus, instead of or in addition to placing the correlating information directly on the ECG record, the data indicative of reference points in the cardiac cycle may be furnished via line 132 from ECG means 122 to the computer and control logic means 110. Thus the said means 110 is actually provided with all three of the essential sources of information, i.e., the raw detector data at 114, the centering signal at 108 and the cardiac phasing signal at 132 which enable storage at means 120 of the entire scan data for the one or more cycles of rotation of apparatus 10, and storage as well of data indicating the correlation of assembly rotational position with the cardiac phases of interest. In other words, appropriate data is now stored at means 120 as will enable an operator subsequent to patient examination, to insert a request at cardiac phase selection means 134, which proceeding via line 136 and computer and control logic means 110, enables read-out from the scan data storage means 120 via line 138, of the projections which will be processed to enable the reconstructed image at display means 116 corresponding to the selected cardiac phase.

The manner in which the projection data is selected for reassemblage pursuant to the present invention, is best understood by reference to FIG. 4 herein, schematically illustrating the collection of suitable projection data by reference to the ECG record 126 in FIG. 3.

In FIG. 4, the cardiac trace shown in simplified schematic fashion at 140, depicts a series of successive "beats," with successive R-waves carrying indicia such as "1," "2," etc. Immediately beneath the cardiac record 144, are seen the indicia marks 130, indicating as already discussed that the scanner 48 has reached its "top dead center" position as previously discussed. In a representative operation pursuant to the invention, the scanner assembly may undergo a single rotation in 6 seconds or two full 360 degree rotations in approximately 12 seconds. With a typical patient, this period of two rotations will correspond to approximately 14 full cardiac cycles. To a rough approximation, this would indicate the availability of only 100 projections (i.e., assuming a projection at each 1 degree of assembly rotation) for association with each of seven slices or phases of the cardiac movement. Thus, if one divides the cardiac cycle into approximately seven phases (which is a useful representative division) then only about 100 projections are actually available for reconstructing an image corresponding to each said phase.

It has been found in general that 100 projections is however, relatively inadequate for producing an acceptable reconstructed image of the heart or other organ. Here it should be recognized that two countervailing factors are involved. One is the interest in limiting the number of projections to those associated with as small a time duration as possible, i.e., in order to enable maximum "freezing" of the heart action. Weighed against this is the countervailing interest of obtaining sufficient numbers of projections to enable good development of the image, by which is meant the development of good quality data reflecting the density function in the ultimate image. To put this matter directly: One is effectively trading off image quality (in the sense of resolution and density) against blurring of the said image. Pursuant to the present invention, a highly effective technique for such trading off is enabled.

Referring back to FIG. 4 there appears at 142, directly beneath the representation of the ECG trace, a series of indicia which divide the cardiac cycle into successive slices—which are seven in number. Here it should be emphasized that selection of grouping into seven is representative of the present approach. The number of such "slices" can be increased or decreased within the physician's range of interest. At the bottom of FIG. 4, the scanner 101 position during scanning is further indicated in angular terms at 144, i.e., for a complete scanner cycle running from 0 to 360 degrees.

Pursuant now to the approach utilized in the present invention, the projection data utilized to reconstruct, e.g., slice 1 of the cardiac phase, is garnered by collecting in each of the cardiac cycles, the projections corresponding to not only slice 1 as shown at 142, but as well those projections corresponding to slice 2. This is schematically suggested, e.g., at 146, at 148, at 150, etc. Further, it will be noted that in reconstructing the image corresponding to slice 2, i.e., slice 2 as defined at 152 in the Figure, the projection data actually utilized, that is the projection data collected, will include not only the projections from slice 2, but also those from the adjacent slice 3—this point being illustrated in the Figure by the schematic showing at 154, 156, 158, etc.

Particularly to be thus noted is that the slices defined at 142 wherein association is made of projections, are processed pursuant to the invention so that in reconstruction of slice 1, the projections from 1 and 2 are used; in reconstruction of slice 2, the projections from slices 2 and 3 are used; etc. In each instance the reconstructed slices are thus utilizing data from an adjacent slice—but further the scheme is such that half of the projections in each reconstructed slices are common with the preceding reconstructed slice, and the other half of such data is common with the next reconstructed slice. The scheme is therefore such that for a given mode of operation, i.e., rate of rotation and gathering of data, etc., and assuming division of the cardiac cycle into a selected number of slices, the number of available projections is effectively doubled. The net effect of this arrangement is therefore one of providing fully acceptable images in terms of blurring, while at the same time providing very acceptable image qualities in terms of density and resolution.

It will of course be understood that the method described in connection with FIG. 4 is precisely similar where the automated techniques described in connection with FIG. 3 are utilized, i.e., in the technique when automated one reads out from the scanner data store 120, those projections corresponding to adjacent slices as just described. Such data is then provided to the computer and control logic means 110, where it is processed in accordance with the convolution and back projection techniques which are fully disclosed in the Pavkovich et al applications previously referenced herein, to ultimately provide an image or display 116 which can be on a CRT or is otherwise available for differing representations, e.g., by photographs or so forth.

When the data is taken throughout the full cycle of an object's cyclic movement the data can be reconstructed into one or more "still" cross-sectional pictures depicting conditions at one or more portions or phases of the cycle. In addition the invention also comprises rapidly presenting cross-sections of sequential positions of the object throughout its cycle of movement, for example, sequential presentation of the 7 phases of the cardiac cycle shown in FIG. 4. The resulting animated presentation of the cyclic movement permits the viewer to detect information which may not be discernable from observation of "still" cross-sectional views. The animated presentation can be directly on the display means 116, or copies of the cross-sections at the various phases can be made and presented with a cine projector.

A somewhat modified aspect of the invention comprises taking data during the occurrence of just one phase or a relatively small number of phases of the cardiac cycle. For example, if one knows in advance that the only phase of interest is phase 2, the computer and control logic 110 is connected to source 50 via line 160 to provide selective control for pulsing of the source. Thus instead of pulsing the source on at each one degree increment for collection of data throughout the cardiac cycle, the computer and control logic 110 is programmed to pulse the source on only during the times the cardiac cycle is in phase 2. If more data is desired for improved image quality the selected pulsing can occur during phases 2 and 3. Also it should be pointed out that the patient is exposed to much reduced radiation during, for example, two revolutions of selective pulsing compared to two revolutions of continuous pulsing.

While the present invention has been particularly set forth in terms of specific embodiments thereof, it will be understood in view of the present teaching, that numerous variations upon the invention are now enabled to those skilled in the art, which variations yet reside within the scope of the present invention. Accordingly, the invention is to be broadly construed and limited only by the scope and spirit of the claims now appended hereto.

We claim:

1. A method for reconstructing images of static cross-sections corresponding to any selected phase in the motion of the heart or of other bodily organs or similar objects undergoing cyclic displacements; said method comprising: positioning the said object to be examined for scanning by the rotational scanning apparatus of a computed tomography scanning system including image reconstruction means;

scanning said object with said scanning apparatus during continuous rotational movement of the scanning apparatus, said scanning being accomplished irrespective of the cyclic displacement of said object occurring at the time of said scanning, and storing the thereby generated scan projection data;

correlating the phase of said object's cyclic displacement sought to be reconstructed with the associated data projections which are at least partially coincident in time with said phase; and reconstructing a desired image at any phase throughout the complete displacement cycle of said object from said associated data projections.

2. A method in accordance with claim 1 wherein said object undergoing examination is a pulsating heart; and wherein said correlation of said data projection with said cyclic phases is affected by correlating the angular position of the scanning apparatus with an ECG signal operatively associated with said heart for thereby correlating said cardiac phases with the said projections at least partially associated therewith.

3. A method in accordance with claim 2 wherein correlation between the position of said scanning apparatus and said ECG signal is affected by developing a positioning signal indicative of a pre-selected angular position for said scanning apparatus and marking the ECG signal record coincident in time with the occurrence of said positioning signal.

4. A method in accordance with claim 2 including storing said ECG signal and storing said positioning signal in a form indicative of its relationship in time to said ECG signal; and reading out said stored signals and utilizing same for assembling the said data projections which are at least partially coincident in time with said selected phase image to be reconstructed.

5. A method in accordance with claim 1 wherein said image corresponding with said phase is reconstructed from data projections associatable with said phase and those associatable with at least a second phase proceeding or following in time said phase.

6. A method in accordance with claim 5 including for each reconstructable phase, operating on projections from said phase and from a second phase adjacent in time to said phase, whereby any two of said reconstructed images corresponding to adjacent phases are reconstructed at least partially from projections common to each reconstruction; thereby enabling an increase in number of projections utilized in said reconstructions.

7. A method in accordance with claim 1 comprising reconstructing an image for each of a plurality of data projections and rapidly presenting said images in sequence.

8. A system for reconstructing images of selected static cross-sections corresponding to selected phases in the motion of a pulsating heart, comprising in combination:

a source of examining radiation and means adapted for moving said source around an object in a continuous motion;

means for receiving said radiation as attenuated by said object and providing scan projection data representative of the attenuated radiation;

means for causing said source to provide scanning radiation during said continuous movement irrespective of the cyclic displacement of said heart occurring at the time of said scanning radiation;

means for storing the scan projection data acquired by said radiation receiving means in examination of said heart;

ECG means adapted to be operatively associated with said heart and providing a signal indicative of the cardiac cycle;

means for correlating the phase of said heart's cyclic displacement sought to be reconstructed with the data projections which are at least partially coincident in time with said phase, said correlating means including means for correlating the angular position of said source with said ECG signal for correlating said cardiac phases with the said projections at least partially associated therewith; and means for reconstructing a desired image from said associated data projections, said correlating means comprising means for reconstructing the cross-section of said object during any phase throughout the complete displacement cycle of said heart;

said means for correlating the position of said source with said ECG signal including means for developing a positioning signal indicative of a preselected angular position of said source; and means responsive to said positioning signal to mark the ECG signal record coincident in time with the occurence of said positioning signal.

* * * * *